United States Patent

Spranger

(10) Patent No.: US 6,328,789 B1
(45) Date of Patent: Dec. 11, 2001

(54) APPARATUS FOR FILTERING AND DEGASSING BODY FLUIDS, IN PARTICULAR BLOOD FILTER

(75) Inventor: Martin Spranger, Ammerbuch (DE)

(73) Assignee: Jostra AG, Hirrlingen (DE)

( * ) Notice: Subject to any disclaimer, the term of this patent is extended or adjusted under 35 U.S.C. 154(b) by 0 days.

(21) Appl. No.: 09/569,268

(22) Filed: May 11, 2000

Related U.S. Application Data

(63) Continuation of application No. PCT/EP98/06860, filed on Oct. 29, 1998.

(30) Foreign Application Priority Data

Nov. 12, 1997 (DE) .............................................. 197 50 062

(51) Int. Cl.⁷ .................................................. B01D 19/00
(52) U.S. Cl. .............................. 96/179; 96/219; 210/188; 604/4; 604/406
(58) Field of Search ........................ 95/241, 260; 96/219, 96/155, 179, 156; 210/188; 604/4, 405, 406

(56) References Cited

U.S. PATENT DOCUMENTS

| | | | |
|---|---|---|---|
| 3,295,297 | * 1/1967 | Collins | 96/155 |
| 3,854,907 | * 12/1974 | Rising | 96/219 |
| 3,891,416 | * 6/1975 | Leonard et al. | 96/219 |
| 3,993,461 | * 11/1976 | Leonard et al. | 96/179 |
| 4,085,047 | * 4/1978 | Thompson | 210/188 |
| 4,188,948 | 2/1980 | Swinton . | |
| 4,190,426 | 2/1980 | Ruschke . | |
| 4,208,193 | 6/1980 | Munsch et al. . | |
| 4,243,531 | * 1/1981 | Crockett et al. | 96/179 |
| 4,326,957 | * 4/1982 | Rosenberg | 96/219 |
| 4,341,538 | * 7/1982 | Vadnay et al. | 96/219 |
| 4,643,713 | * 2/1987 | Vittala | 96/155 |
| 4,704,203 | * 11/1987 | Reed | 96/179 |
| 4,734,269 | * 3/1988 | Clarke et al. | 96/219 |
| 4,758,337 | 7/1988 | Köhn et al. . | |
| 5,000,764 | * 3/1991 | Oshiyama et al. | 96/219 |
| 5,252,222 | * 10/1993 | Matkovich et al. | 210/188 |
| 5,429,595 | * 7/1995 | Wright, Jr. et al. | 210/188 |
| 5,439,587 | * 8/1995 | Stankowski et al. | 96/219 |
| 5,707,520 | * 1/1998 | Kuroki et al. | 210/188 |
| 6,015,500 | * 1/2000 | Zuk, Jr. | 95/241 |

FOREIGN PATENT DOCUMENTS

| | | |
|---|---|---|
| 28 34 265 A1 | 4/1979 | (DE) . |
| 28 51 838 A1 | 5/1979 | (DE) . |
| 35 41 521 C2 | 1/1989 | (DE) . |
| 196 20 591 A1 | 11/1997 | (DE) . |
| 0 076 421 A2 | 4/1983 | (EP) . |
| 2 231 282 A | 11/1990 | (GB) . |

\* cited by examiner

*Primary Examiner*—Duane S. Smith
(74) *Attorney, Agent, or Firm*—Harness, Dickey & Pierce, P.L.C.

(57) ABSTRACT

An apparatus for filtering and degassing body fluid has two filter chambers, separated from one another by a filter medium. The first filter chamber is connected to an inflow connector, and the second filter chamber to an outflow connector. An aeration and venting device common to the two filter chambers which is connectable selectably and separately to the first or the second filter chamber.

14 Claims, 5 Drawing Sheets

APPARATUS FOR FILTERING AND DEGASSING BODY FLUIDS, IN PARTICULAR BLOOD FILTER

This is a continuation of International patent application Ser. No. PCT/EP98/06860, filed Oct. 29, 1998.

BACKGROUND OF THE INVENTION

1. Field of the Invention

The present invention relates to an apparatus for filtering and degassing body fluids, in particular a blood filter, having at least two filter chambers, separated from one another by a filter medium, that are preferably arranged in a common housing, the first filter chamber being connected to an inflow connector for body fluid that is to be filtered, and the second filter chamber to an outflow connector for filtered body fluid.

2. Related Prior Art

An apparatus of this kind is known from DE 35 41 521 C2.

The known apparatus is a blood filter whose inflow connector, in the operating position, is connected vertically from below to the first filter chamber. The inflow connector leads into a rising tube that passes through the cylindrical first filter chamber to approximately two-thirds of its height. The blood being filtered emerges at the top from the rising tube, which is configured as an overflow, and falls along the outside of the rising tube into a sump.

As these overflows occur, the gas dissolved in the blood is separated out in the form of gas bubbles that rise upward. At the top of the first filter chamber is a gas outlet through which the first filter chamber is vented.

The rising tube is surrounded by a hollow-cylindrical filter medium adjoined externally by a hollow-cylindrical second filter chamber that is equipped at its upper end with a gas outlet opening for venting the second filter chamber.

In the operating position, the second filter chamber is connected at the bottom to a horizontally proceeding outflow connector through which the filtered blood emerges from the known blood filter.

The known blood filter is used for extracorporeal blood circulation systems, in which blood is filtered and purified of gas bubbles before being returned to the patient. This step must not damage the blood cells or trigger any coagulation mechanisms. Blood losses must also be avoided. In the known filter, the separation of particles and aggregates is performed in the form of a dead-end filtration system, although this has the disadvantage that the retained constituents gradually accumulate in the filter. In the case of the known filter, these constituents collect in the sump, as a result of which the filter medium gradually becomes clogged, progressively from bottom to top, by sedimenting particles and aggregates.

In the case of a blood filter incorporated into an extracorporeal blood circulation system, this clogging can result in an undesirable reduction in the volumetric flow of the filtered whole blood, or even in complete interruption of the circulation system and an impermissible rise in pressure across the filter, which has an undesirable effect on the blood constituents.

It is known for this purpose that in the case of a blood filter of the aforesaid kind, a bypass having, for example, two Y-pieces is constructed, the two arms of the two Y-pieces being connected to the blood filter and to a bypass line, respectively the respective upright of the Y-line then forms the inflow or the outflow for the parallel arrangement made up of blood filter and bypass. A shutoff valve is incorporated into the bypass line, although it is also known to interrupt the bypass line using a tubing clamp.

If the blood filter has become impermissibly clogged, the bypass line is opened so that blood circulation can be maintained around the blood filter.

This specific arrangement of the blood filter with bypass line requires greater complexity in terms of equipment as well as special cleaning actions, and is therefore disadvantageous. A further disadvantage with this bypass line is the fact that coagulated blood can collect in the bypass line above the shutoff valve or tubing clamp and, when the bypass line is suddenly opened, can pass into the blood circulation system in the form of a plug and, in unfavorable cases, result in embolisms.

A further disadvantage with the known blood filter is the fact that the two separate vent openings create the need for iterative interventions in order to vent the blood filter completely. Venting of this kind is, however, necessary prior to use of the blood filter in the extracorporeal blood circulation system in order to prevent gas bubbles from getting into the blood circulation system and causing known negative effects.

With the known blood filter, therefore, there exist considerable handling and sterility problems that are associated with the bypass line and with the two venting openings. In addition, the known blood filter exhibits safety risks in use, resulting both from the bypass line and from sedimentation of the separated particles and aggregates.

An additional general disadvantage with the known blood filter is its bulky construction, which results in particular from the fact that the venting space of the inner, first filter chamber is arranged above the rising tube and the second filter chamber.

DE 196 20 591 discloses a more compact apparatus for removing gases from liquids and using the principle of degassing by overflow, known from the blood filter cited above. In this case the overflow connection is provided between a cylindrical inner and a hollow-cylindrical outer filter chamber, the flow space that guarantees the overflow being equipped with a hydrophobic filter that discharges the emerging gas upward but holds back the blood. With this apparatus the blood itself is not passed through a filter medium, so this is therefore not a blood filter.

A further, very special and not universally applicable filter for hemofiltration or plasmapheresis, i.e. in which there is a large pressure drop across the filter medium, is known from EP 0 076 421. This filter comprises an inner and an outer fiber bundle, connected respectively to an inlet connection and outlet connection. There is also a filtrate outlet; in other words this is not a dead-end filter but rather a crossflow filter, with a corresponding blood loss.

Arranged between the inlet and the outlet is a kind of pressure relief valve that automatically creates a connection between the inlet and outlet if the pressure drop across the series-connected fiber bundles becomes too great.

For safety reasons, this filter is of only limited suitability for use in extracorporeal blood circulation systems. One disadvantage of the filter is the fact that activation of the pressure relief valve is not visible, so that operating personnel cannot detect whether the filter is clogged or is still working satisfactorily. In addition, the pressure relief valve creates the risk of inadvertent opening and of leakage flows. The reason is that in specific pressure ranges, it opens only partially; and the opening pressure cannot be established reproducibly because of aging and stress processes and fluctuations in the properties of the materials used.

A further disadvantage of this filter is that it "cycles," i.e. after opening in response to an impermissibly high pressure rise across the filter medium, that pressure then usually drops again, so that the pressure relief valve closes again; this then in turn results in a pressure buildup that opens the pressure relief valve again.

SUMMARY OF THE INVENTION

In view of this prior art, it is an object of the present invention to further develop the apparatus mentioned at the outset in such a way that the above disadvantages are eliminated with a simple physical construction and a small design, resulting in particular in easy and reliable handling with operation that is safe for the patient.

In the case of the apparatus mentioned at the outset, this object is achieved according to the present invention in that an aeration and venting device common to both filter chambers, which is connectable selectably and separately to the first and to the second filter chamber, is provided.

The object underlying the invention is completely achieved in this fashion.

Specifically, the inventor of the present application has recognized that it is possible, in particular by way of physical features yet to be described, to provide a common vent for both filter chambers so that the two chambers can be vented separately and selectably. It is thereby possible, simply by manipulating, for example, a valve of the new apparatus, to vent first an outer filter chamber that fills up more quickly with body fluid, and then, by a simple pivoting action, an inner filter chamber that subsequently fills up completely. In addition to simple manipulation, however, the common aeration and venting device also has design advantages, since provision needs to be made for sealing only a single venting device. A further advantage is the fact that the risk of contamination at or through the aeration device is limited to a single aeration and venting device.

In an embodiment, it is preferred if there is provided between the inflow and outflow connectors, which preferably are arranged adjacent to one another at the point on the apparatus that is lowest in the operating position, a connecting element by way of which the inflow and outflow connectors can selectably be connected directly to one another, bypassing the filter medium.

This feature greatly improves the operating reliability of the new apparatus, since it results in the creation of a selectably switchable bypass so that the bypass line necessary in the prior art, with the disadvantages and problems associated therewith, can be dispensed with. On the one hand, the "integrated bypass line" reduces complexity in terms of equipment; on the other hand, the accumulation of coagulated blood and aggregates is prevented, greatly diminishing the risk of embolism.

This feature thus also, however, achieves the object of the invention separately—i.e. without the common aeration and venting device—in the case of the generic blood filter cited at the outset, and is of itself inventive.

It is further preferred if flow directing means, which divide the incoming body fluid into at least a first subflow flowing onto the filter medium from below in the operating position, and at least one further subflow flowing onto the filter medium approximately centeredly, are provided in the first filter chamber.

The advantage of this feature is that clogging of the filter medium rising gradually from below is prevented, since the first subflow that is not provided in the prior art, flowing onto the filter medium from below reimparts turbulence to the sediments, so that the entire filter surface is available for filtration of the body fluid. The inventor of the present application has recognized that this feature results in an approximately homogeneous distribution of the filter residues in the first filter chamber where turbulence is imparted to these particles, so that contrary to expectations, the filtering effect and the flow capacity of the filter are reduced much less over time than in the case of a generic blood filter.

In addition, however, this feature therefore achieves the object of the invention in the context of the generic apparatus when considered of itself, i.e. without the common aeration and venting device and the integrated bypass. This feature as well is therefore inventive when considered of itself in the context of the generic apparatus.

In particular, however, the combination of the three features so far described results in a very easy-to-handle and very reliably operating filter for body fluids that is moreover of simple physical construction and has a small, compact design.

In an embodiment, it is preferred if the housing has a prismatic shape with preferably a square cross section, and if the aeration and venting device is arranged at one corner of the housing.

The advantage of this feature is that the gas collects in the tip formed at the top in the operating state, thus making possible efficient aeration and venting, in particular during refilling. A further advantage is the compact arrangement as well as the large square base outline of the new apparatus available for the filtering effect.

It is further preferred if the aeration and venting device comprises a rotatably mounted hollow cylinder whose outward-leading inner channel can be selectably connected to one of the two filter chambers by rotating the hollow cylinder.

This feature is advantageous in terms of design: a single hollow cylinder mounted rotatably on the housing makes possible separate and selectable venting of both filter chambers. A further advantage of this arrangement is that it is easy to sterilize and can be arranged without difficulty in a corner of the housing.

It is further preferred if the outflow connection comprises a tube segment that extends in the first filter chamber transversely above the inflow connector, preferably as a flow directing means.

This feature also is advantageous in terms of design: the tube segment serves on the one hand as an outflow for the filtered body fluid and on the other hand to distribute the inflowing body fluid, so that the latter is distributed homogeneously over the filter medium; in addition, provision can further be made for flow to arrive at the filter medium from below.

In an embodiment, the tube segment is rotatably mounted and has an outward-leading bore whose inner opening can selectably be connected, by rotation, to the second filter chamber or to the inflow connector, so that the tube segment acts as a connecting element.

This feature also is advantageous in terms of design, since the tube segment performs, as a further function, that of the integrated bypass. A further advantage is the fact that the flow of body fluid passes through the bore of the tube segment both in filter mode and in bypass mode, so that no coagulating blood or other aggregates can collect and possibly lead to a risk of embolism when switching over to bypass mode.

It is preferred in general if the second filter chamber comprises at least two parallel subchambers of flat configuration that are arranged in the first filter chamber and are separated from it on both sides by filter medium.

This feature allows a compact configuration for the new apparatus, since a large area of the filter medium is available, in a small space, for the filtering effect. In addition, such subchambers of the second filter chamber arranged parallel to one another can yield favorable flow conditions which impart turbulence to the sediments, so that this feature as well effectively prevents clogging of the filter medium in general.

It is preferred in this context if the filter medium is configured as a nonwoven fabric or a wire gauze or sieve fabric, and is attached to supporting plates or frames in such a way that gas bubbles cannot be captured, the filter medium preferably being supported by support elements, preferably webs or knobs, that are aligned vertically when the apparatus is in the operating position.

This feature allows rapid venting of the new apparatus, since gas bubbles cannot get caught on ribs or other support elements for the filter. It is known from practical experience that when filters are vented, the housing must be repeatedly tapped in order to detach gas bubbles that adhere to any internal support elements in the filter. The inventor named in the present application has now recognized that by way of the features described here, it is possible simply by design means to prevent gas bubbles from collecting in the filter at all. This is assisted by the use of a flat nonwoven fabric or sieve fabric which, in contrast to the pleated filter media used in the aforementioned DE 35 41 521 C2, effectively prevents not only the accumulation of gas bubbles in or on the filter medium, but also the accumulation of aggregates or other sediments. The reason is that because flow arrives at the filter medium from below both upon initial filling and in filtering mode, the subflow of body fluid rising from below ensures that any adhering sediments of gas bubbles are effectively removed from the filter surface. This ensures good venting and an effective filtering action.

Lastly, it is also preferred if the flow directing means comprise flow panels that are arranged parallel to narrow sides of the housing.

This feature also contributes to effective distribution of the subflows in the new apparatus, so that the body fluid is made turbulent in the new apparatus, both upon initial filling and during operation, in such a way that despite the features described above, adhering gas bubbles and/or sediments in the filter are detached.

Further advantages are evident from the description and the appended drawings.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention is shown in the drawings and will be explained in more detail in the description below. In the drawings.

DETAILED DESCRIPTION OF A PREFERRED EMBODIMENT

Figure 1:
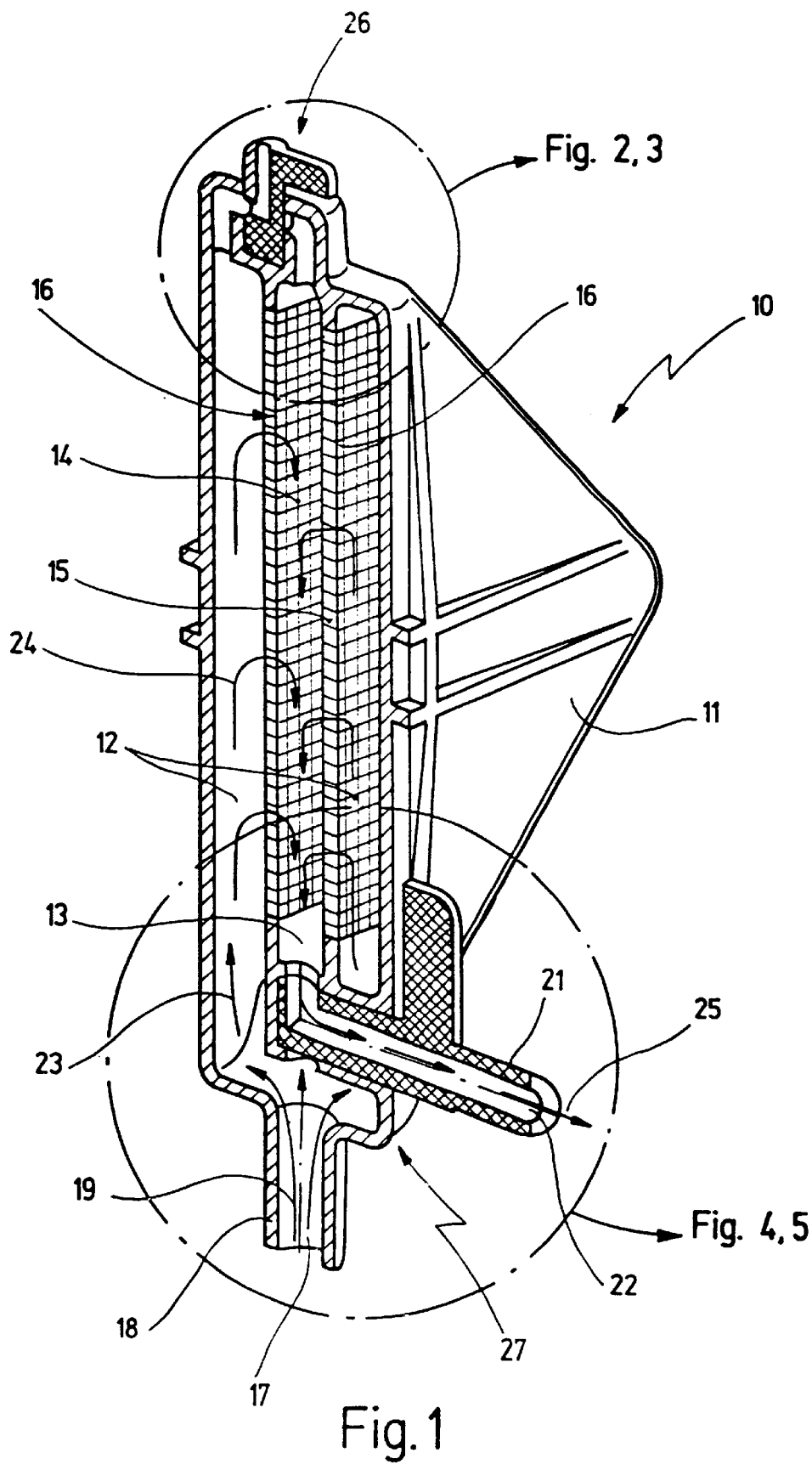
FIG. 1 shows a perspective view of a longitudinally sectioned embodiment of the apparatus.

FIG. 1 shows, in a perspective longitudinal section, an apparatus 10 for filtering and degassing body fluid, which in the selected embodiment is a blood filter. Apparatus 10 is configured as a dead-end filter, so that (in contrast to crossflow filters) blood loss during use is avoided.

Apparatus 10 comprises a prismatic housing 11 in which a first filter chamber 12 and a second filter chamber 13 are arranged.

Second filter chamber 13 is delimited by two side walls 14, 15, respectively fitted with a filter medium 16 that separates first filter chamber 12 from second filter chamber 13.

At its point that is lowest in the operating position shown in FIG. 1, apparatus 10 has an inlet 17 at an inflow connector 18, through which a body fluid flow indicated at 19 passes into first filter chamber 12. Located directly adjacent to inflow connector 19 is an outflow connector 21 with an outlet 22.

Body fluid flow 19 passing into apparatus 10 rises upward in first filter chamber 12, as indicated by an arrow 23, and passes laterally through filter medium 16 into second filter chamber 13, as indicated by arrows 24. In second filter chamber 13, the body fluid drops downward and emerges from outlet 22 again as filtered body fluid, as indicated by an arrow 25.

At its upper end, apparatus 10 has a common aeration and venting device 26 for first and second filter chambers 12, 13, a connecting element 27 being provided, at its end remote from the upper end, between inflow connector 18 and outflow connector 21.

Figure 3:
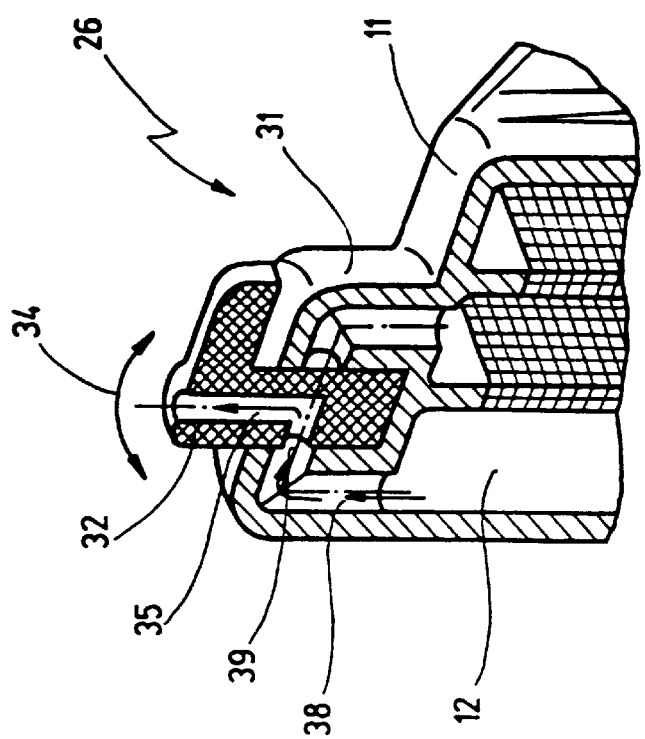
FIG. 3 shows the aeration and venting device of FIG. 2 in a second operating state.
Figure 2:
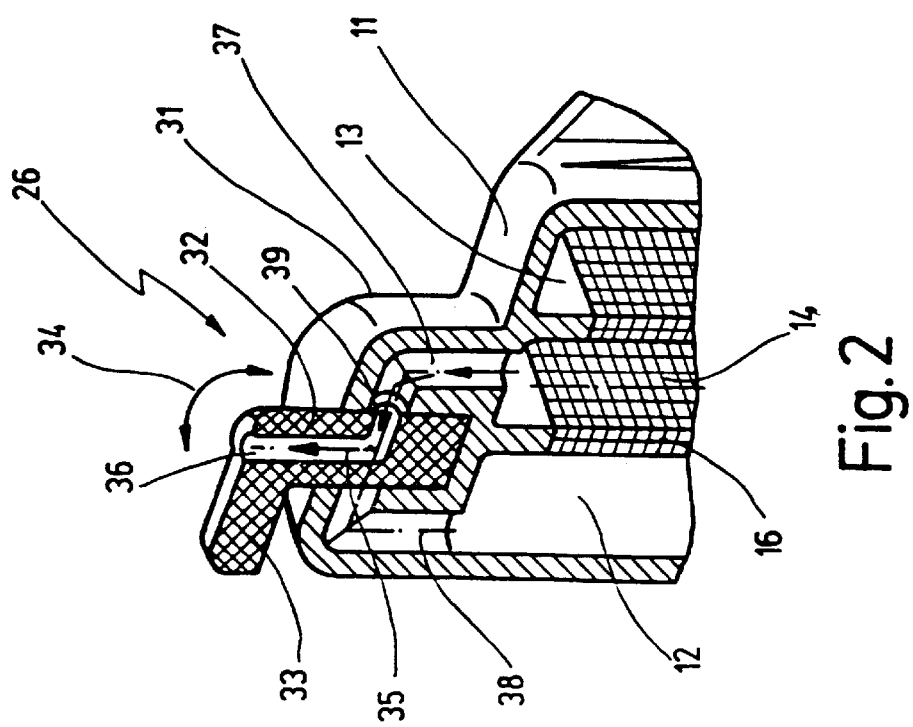
FIG. 2 shows an enlarged detail view of the aeration and venting device of the apparatus of FIG. 1, in a first operating state.

Common aeration and venting device 26 is shown in FIGS. 2 and 3 in an enlarged longitudinal section. Aeration and venting device 26 is arranged at an upper corner 31 of housing 11 and comprises a hollow cylinder 32, mounted rotatably in housing 11, that can be pivoted by way of a lever 33 in the direction of an arrow 34.

A laterally open inner channel 35, whose outlet 36, open at the top, allows gas to emerge, is provided in hollow cylinder 32.

An upward-pointing rising channel 37 leads from second filter chamber 13, and an upward-pointing rising channel 38 leads from first filter chamber 12, to hollow cylinder 32, whose lateral opening 39 communicates with rising channel 37 in the operating state of FIG. 2, and with rising channel 38 in the operating state of FIG. 3.

It is thereby possible, by simply rotating lever 33, initially to vent first filter chamber 12 as apparatus 10 is filled with body fluid, and then to vent second filter chamber 13; in a third operating position (not shown in the Figures), lever 33 is in a position 90 degrees between the positions shown in FIGS. 2 and 3, so that opening 39 is closed off and no further body fluid can emerge from outlet 36.

The simple design of aeration and venting device 26 makes possible not only simple handling but also simple cleaning and sterilization.

Figure 5:
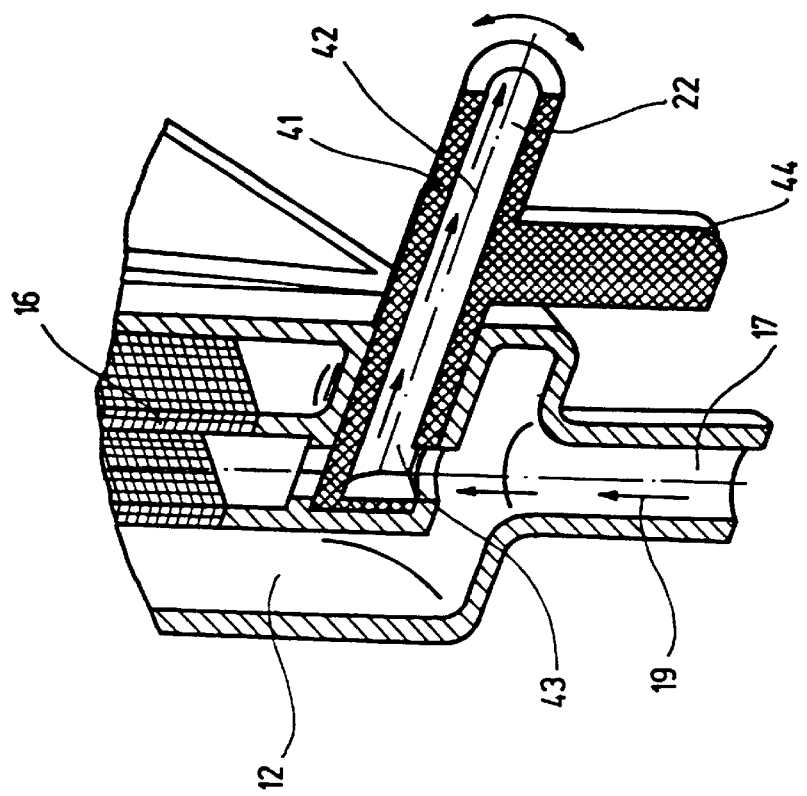
FIG. 5 shows, in a view like that of FIG. 4, the connecting element in a second operating state.
Figure 4:
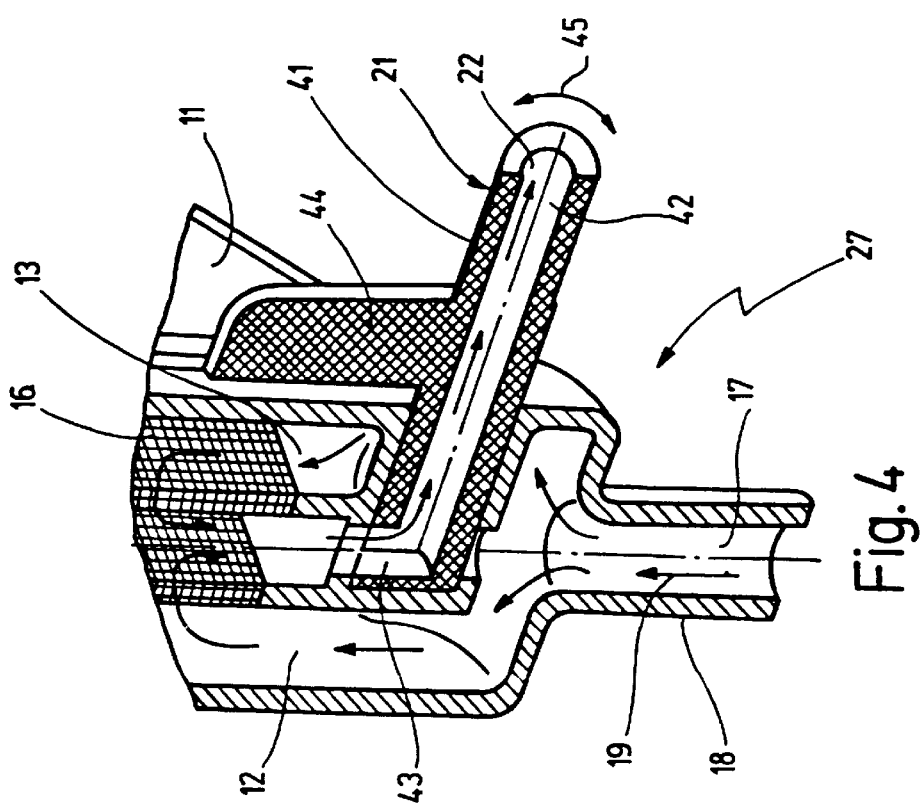
FIG. 4 shows an enlarged detail view of the connecting element of the apparatus of FIG. 1, in a first operating state.

FIGS. 4 and 5 show connecting element 27, located at the lower end of housing 11, which comprises a tube segment 41, mounted rotatably in housing 11, whose bore 42 opens in the interior of housing 11 into a laterally proceeding opening 43.

Attached to tube segment 41 is a lever 44 with which tube segment 41 is pivotable through 180 degrees, as indicated by an arrow 45.

In the operating position shown in FIG. 4, opening 43 is in communication with second filter chamber 13 so that filtered body fluid can pass into bore 42 and from there to outlet 22.

In the other operating position shown in FIG. 5, on the other hand, opening 43 is connected directly to inlet 17, so that body fluid flow 19 emerges directly from outlet 22, bypassing filter medium 16.

This "integrated bypass" makes it possible, without further bypass tubes or connecting clamps, to switch apparatus 10 selectably into an extracorporeal blood circulation system or, so to speak, to short-circuit the filter medium if it is clogged or if the filter function is no longer needed.

Figure 6:
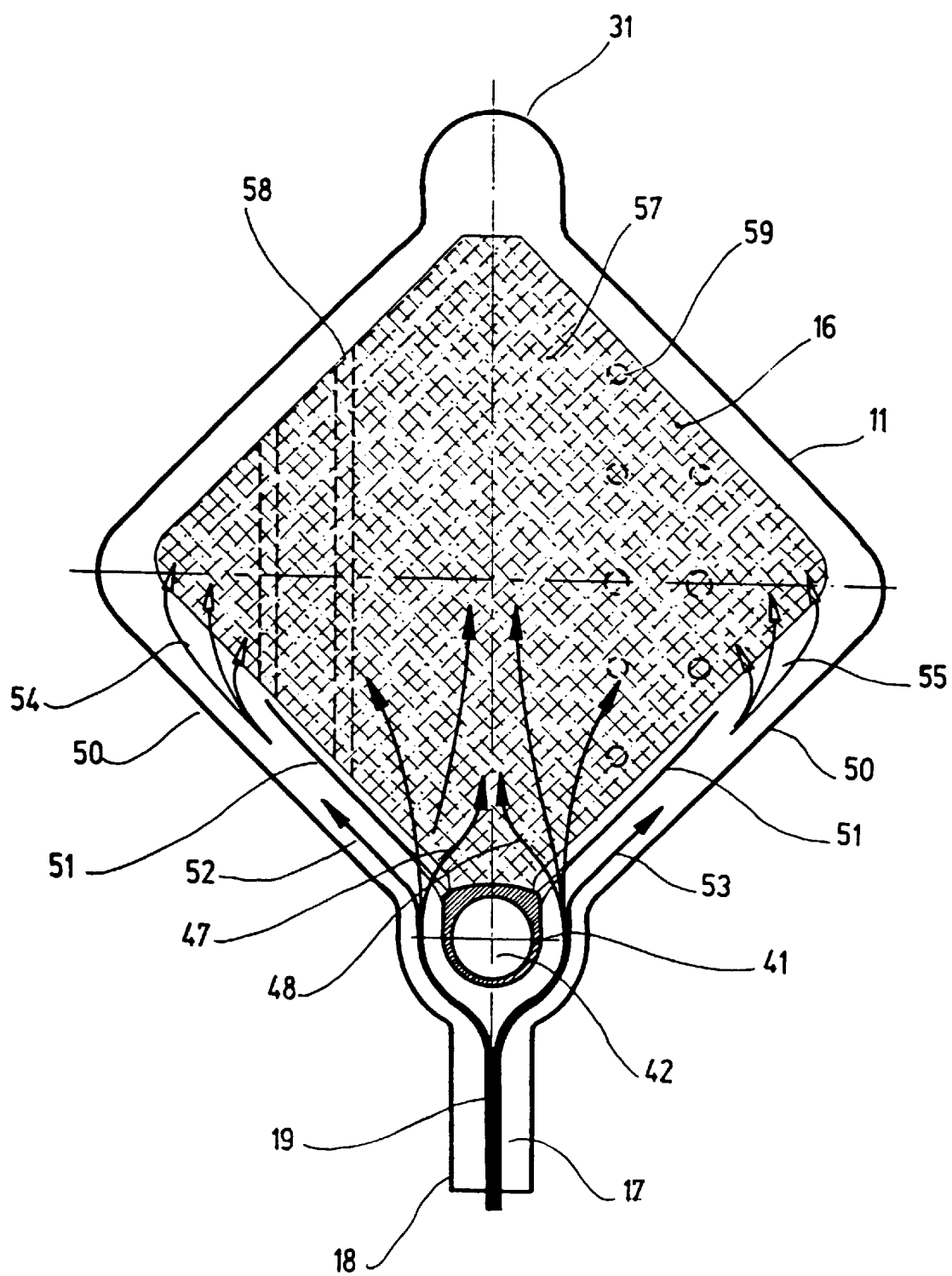
FIG. 6 shows a plan view of the apparatus of FIG. 1 in cross section.

It is also evident from FIGS. 4 and 5 that tube segment 41 extends transversely above inflow connector 18 in such a way that it lies directly in body fluid flow 19 and divides the latter into subflows, as is more easily visible in the sectioned plan view of FIG. 6.

Subflows 47 and 48 produced by tube segment 41 pass by tube segment 42 to the left and right and arrive at filter medium 16 from below in FIG. 6. As shown in FIG. 6, housing 11 is square in plan; provided on its two lower narrow sides 50 are two flow panels 51 which direct subflows 52 and 53 laterally upward where, as subflows 54 and 55, they strike filter medium 16 approximately centeredly.

Tube segment 41 and flow panels 51 form, so to speak, flow directing means by way of which body fluid flow 19 is divided into different subflows that flow onto filter medium 16 partly from below and partly approximately centeredly from the side; further subflows not shown in FIG. 6, which flow onto filter medium 16 even farther up, also occur.

This distribution of the subflows imparts turbulence to the sediments, so that filter medium 16 cannot—as in the prior art—slowly and increasingly clog up from bottom to top.

Filter medium 16 is a nonwoven fabric 57 that rests on vertically oriented webs 58 or knobs 59 that serve as support elements for nonwoven fabric 57 and determine the interior width of second filter chamber 13.

Figure 7:
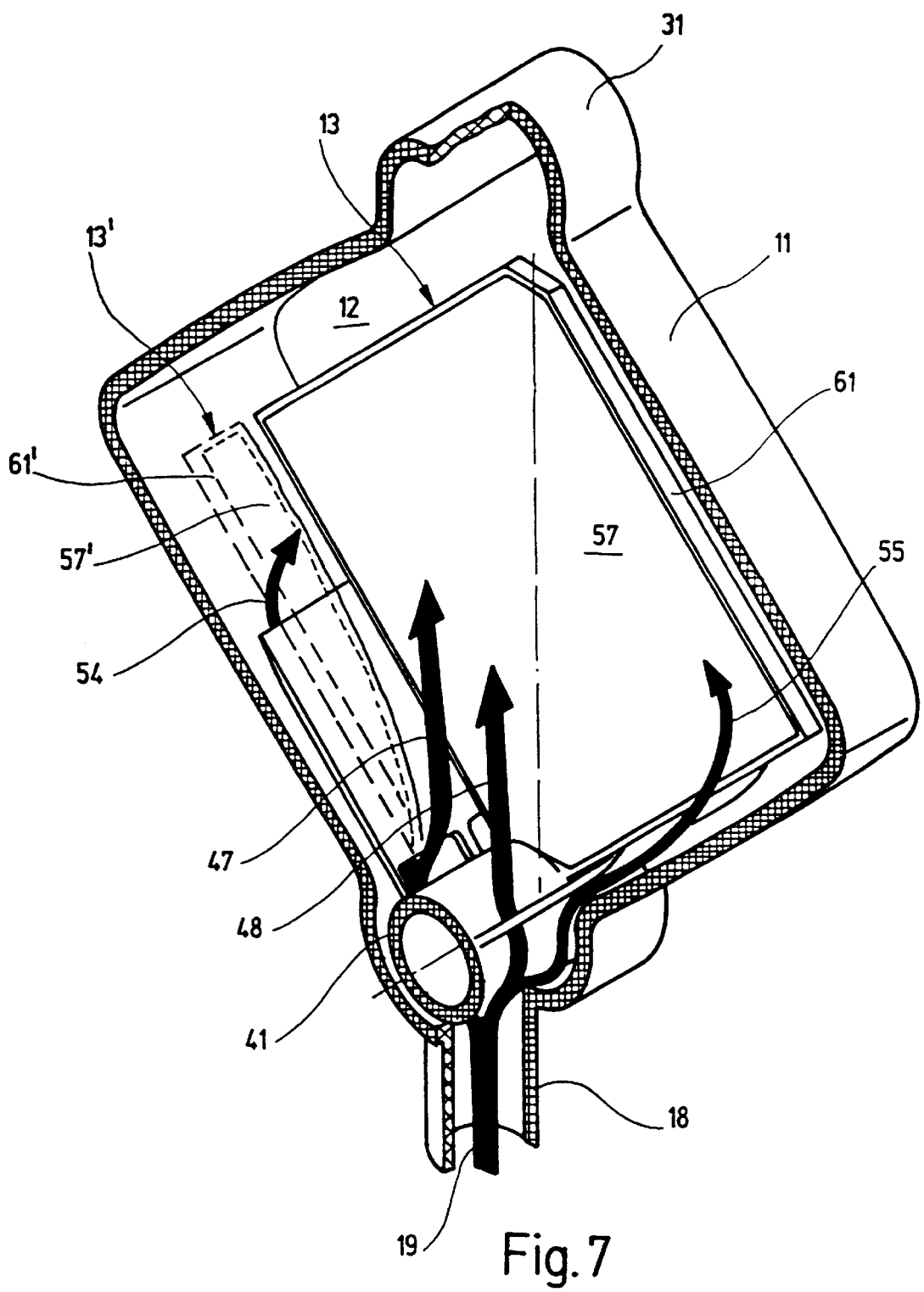
FIG. 7 shows a perspective view of the apparatus of FIG. 6.

To increase the filter area it is possible to use, instead of one second filter chamber 13, several filter chambers 13, 13' of flat configuration arranged in parallel next to one another, as indicated in FIG. 7. Each individual filter chamber 13, 13' comprises a support frame 61, 61' on which nonwoven fabric 57, 57' is respectively stretched, being supported by support elements 58 or 59 known from FIG. 6 so as to maintain the interior width of second filter chamber 13, 13' over the entire surface.

The distribution of subflows 47, 48, 54, 55, which provide effective utilization of the entire surface of filter medium 16, is shown again in FIG. 7.

Therefore, what I claim is:

1. An apparatus for filtering and degassing body fluid, having
   a first and a second filter chamber,
   a filter medium separating said first and second filter chambers from one another,
   the first filter chamber connected to an inflow connector for body fluid to be filtered,
   the second filter chamber connected to an outflow connector for filtered body fluid, and
   an aeration and venting device that is connectable selectably and separately to the first and the second filter chamber, respectively.

2. An apparatus as in claim 1, further comprising a connecting element provided between the inflow and outflow connectors and arranged such as to selectably interconnecting the inflow and outflow connectors, thus bypassing the filter medium.

3. An apparatus as in claim 2, wherein said inflow and outflow connectors are arranged adjacent to one another at a point of the apparatus that is lowest in its operation position.

4. An apparatus as in claim 1, wherein flow directing means are provided in the first filter chamber and arranged such as to divide body fluid entering the first filter chamber via the inflow connector at least in a first subflow flowing into the filter medium from below in the operating position and at least one further subflow flowing onto the filter medium approximately centeredly.

5. An apparatus as in claim 1, wherein the first and second filter chambers are arranged with a common housing, the housing having a prismatic shape with a square cross section, and the aeration and venting device is arranged at one corner of the housing.

6. An apparatus as in claim 1, wherein the aeration and venting device comprises a rotatably mounted hollow cylinder whose outward-leading inner channel can be selectably connected to one of the two filter chambers by rotating the hollow cylinder.

7. An apparatus as in claim 1, wherein the outflow connection comprises a tube segment that extends in the first filter chamber transversely above the inflow connector, preferably as a flow directing means.

8. An apparatus as in claim 7, wherein the tube segment is rotatably mounted and has an outward-leading bore whose inner opening can selectably be connected, by rotation, to the second filter chamber or to the inflow connector, so that the tube segment acts as a connecting element.

9. An apparatus as in claim 1, wherein the second filter chamber comprises at least two parallel subchambers of flat configuration that are arranged in the first filter chamber and are separated from it on both sides by filter medium.

10. An apparatus as defined in claim 1, wherein the filter medium is configured as a nonwoven fabric or sieve fabric, and is attached to supporting plates or frames in such a way that gas bubbles cannot be captured.

11. An apparatus as in claim 1, wherein the filter medium is supported by support elements, preferably webs or knobs, that are aligned vertically when the apparatus is in the operating position.

12. An apparatus as in claim 3, wherein the flow directing means comprise flow panels that are arranged parallel to narrow sides of the housing.

13. An apparatus for filtering and degassing body fluid, having
    a first and a second filter chamber, a filter medium separating said first and second filter chambers from one another, the first filter chamber connected to an inflow connector for body fluid to be filtered, the second filter chamber connected to an outflow connector for filtered body fluid, further comprising a connecting element provided between the inflow and outflow connectors and arranged such as to selectably interconnecting the inflow and outflow connectors, thus bypassing the filter medium.

14. An apparatus for filtering and degassing body fluid, having a first and a second filter chamber, a filter medium separating said first and second filter chambers from one another, the first filter chamber connected to an inflow connector for body fluid to be filtered, the second filter chamber connected to an outflow connector for filtered body fluid, wherein flow directing means are provided in the first filter chamber and arranged such as to divide body fluid entering the first filter chamber via the inflow connector at least in a first subflow flowing into the filter medium from below in the operating position and at least one further subflow flowing onto the filter medium approximately centeredly.

* * * * *